(12) United States Patent
Cooks et al.

(10) Patent No.: US 11,984,311 B2
(45) Date of Patent: May 14, 2024

(54) MASS SPECTROMETRY VIA FREQUENCY TAGGING

(71) Applicant: Purdue Research Foundation, West Lafayette, IN (US)

(72) Inventors: Robert Graham Cooks, West Lafayette, IN (US); Dalton Snyder, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 520 days.

(21) Appl. No.: 17/284,144

(22) PCT Filed: Oct. 8, 2019

(86) PCT No.: PCT/US2019/055112
§ 371 (c)(1),
(2) Date: Apr. 9, 2021

(87) PCT Pub. No.: WO2020/076765
PCT Pub. Date: Apr. 16, 2020

(65) Prior Publication Data
US 2021/0335592 A1   Oct. 28, 2021

Related U.S. Application Data

(60) Provisional application No. 62/743,600, filed on Oct. 10, 2018.

(51) Int. Cl.
*H01J 49/42* (2006.01)
*G01N 33/68* (2006.01)
*H01J 49/02* (2006.01)

(52) U.S. Cl.
CPC ...... *H01J 49/4225* (2013.01); *G01N 33/6848* (2013.01); *H01J 49/025* (2013.01); *H01J 49/429* (2013.01)

(58) Field of Classification Search
CPC .... H01J 49/4225; H01J 49/025; H01J 49/429; H01J 49/427; H01J 49/005; G01N 33/6848
See application file for complete search history.

(56) References Cited

U.S. PATENT DOCUMENTS

| | | | | |
|---|---|---|---|---|
| 5,248,882 A | * | 9/1993 | Liang | H01J 49/38 250/282 |
| 5,457,315 A | * | 10/1995 | Wells | H01J 49/424 250/282 |
| 5,517,025 A | * | 5/1996 | Wells | H01J 49/427 250/282 |

(Continued)

FOREIGN PATENT DOCUMENTS

| | | | | |
|---|---|---|---|---|
| GB | 2532533 A | * | 5/2016 | G01N 27/622 |
| WO | 2009/102766 A1 | | 8/2009 | |
| WO | WO-2014208336 A1 | * | 12/2014 | H01J 49/423 |

OTHER PUBLICATIONS

Bonner, 1977, The Cylindrical Ion Trap, International Journal of Mass Spectrometry and Ion Physics, 24(3):255-269.

(Continued)

*Primary Examiner* — David A Vanore
(74) *Attorney, Agent, or Firm* — Brown Rudnick LLP; Adam M. Schoen

(57) ABSTRACT

The invention generally relates to mass spectrometry via frequency tagging.

1 Claim, 16 Drawing Sheets

(56) References Cited

U.S. PATENT DOCUMENTS

| | | | | |
|---|---|---|---|---|
| 5,608,216 | A * | 3/1997 | Wells | H01J 49/427 250/282 |
| 5,644,131 | A * | 7/1997 | Hansen | H01J 49/424 313/256 |
| 6,838,666 | B2 * | 1/2005 | Ouyang | H01J 49/422 250/282 |
| 7,335,897 | B2 * | 2/2008 | Takats | H01J 49/142 250/288 |
| 7,456,396 | B2 * | 11/2008 | Quarmby | H01J 49/427 250/288 |
| 8,304,718 | B2 * | 11/2012 | Ouyang | H01J 49/0422 250/281 |
| 9,460,900 | B2 * | 10/2016 | Bonner | H01J 49/0031 |
| 9,666,420 | B2 * | 5/2017 | Giuliani | H01J 49/4225 |
| 10,141,174 | B2 * | 11/2018 | Aliman | H01J 49/4295 |
| 10,852,306 | B2 * | 12/2020 | Coon | H01J 49/04 |
| 11,127,581 | B2 * | 9/2021 | Cooks | H01J 49/429 |
| 2006/0038123 | A1 * | 2/2006 | Quarmby | H01J 49/427 250/282 |
| 2008/0135747 | A1 * | 6/2008 | Brekenfeld | H01J 49/42 250/283 |
| 2009/0299671 | A1 * | 12/2009 | Jones | H01J 49/0031 702/85 |
| 2012/0119079 | A1 * | 5/2012 | Ouyang | H01J 49/16 250/288 |
| 2012/0205535 | A1 * | 8/2012 | Lemoine | G01N 33/6848 250/282 |
| 2016/0071709 | A1 * | 3/2016 | Hendricks | H01J 49/009 250/282 |
| 2021/0013023 | A1 * | 1/2021 | Cooks | H01J 49/0081 |
| 2021/0225625 | A1 * | 7/2021 | Cooks | H01J 49/004 |
| 2021/0305034 | A1 * | 9/2021 | Fujimoto | H01J 49/0027 |
| 2021/0335592 | A1 * | 10/2021 | Cooks | H01J 49/4225 |

OTHER PUBLICATIONS

Carroll, 1975, Atmospheric Pressure Ionization Mass Spectrometry: Corona Discharge Ion Source for Use in Liquid Chromatograph-Mass Spectrometer-Computer Analytical System, Anal. Chem. 47:2369-2373, published in USA.

Cody, 2005, Versatile new ion source for the analysis of materials in open air under ambient conditions, Anal. Chem., 77:2297-2302.

Fenn, 1989, Electrospray Ionization for Mass Spectrometry of Large Biomolecules, Science 246:64-71.

Gao et al., 2006, Handheld rectilinear ion trap mass spectrometer, Anal. Chem., 78:5994-6002.

Gao, 2008, Design and Characterization of a Multisource Hand-Held Tandem Mass Spectrometer, Z. Anal. Chem, 80:7198-7205.

Hagar, 2002, A new linear ion trap mass spectrometer, Rapid Communications in Mass Spectrometry, 16(6):512-526.

Hendricks, 2014, Autonomous in-situ analysis and real-time chemical detection using a backpack miniature mass spectrometer: concept, instrumentation development, and performance, Anal. Chem., 86:2900-2908.

Hou, 2011, Sampling wand for an ion trap mass spectrometer, Anal Chem., 83:1857-1861.

Kogelschatz, 2003, Dielectric-Barrier Discharges: Their History, Discharge Physics, and Industrial Applications, Plasma Chemistry and Plasma Processing, 23:1-46.

Laiko, 2000, Atmospheric Pressure Matrix-Assisted Laser Desoprtion/Ionization Mass Spectrometry, Analytical Chemistry, 72:652-657.

Li, 2014, Mini 12, Miniature Mass Spectrometer for Clinical and Other Applications-Introduction and Characterization, 86(6):2909-2916.

Schwartz, 2002, A two-dimensional quadrupole ion trap mass spectrometer, J. Am. Soc. Mass Spectrom., 13:659-669.

Shiea, 2005, Electrospray-assisted laser desorption/ionization mass spectrometry for direct ambient analysis of solids, J. Rapid Communications in Mass Spectrometry, 19:3701-3704.

Snyder, 2016, Calibration procedure for secular frequency scanning in ion trap mass spectrometers, Rapid Commun. Mass Spectrom, 30(10):1190-1196.

Snyder, 2017, Single Analyzer Neutral Loss Scans in a Linear Quadrupole Ion Trap Using Orthogonal Double Resonance Excitation, Anal. Chem., 89(15):8148-8155.

Sokol, 2011, Miniature mass spectrometer equipped with electrospray and desorption electrospray ionization for direct analysis of organics from solids and solutions, Int. J. Mass Spectrom., 306(2-3):187-195.

Takats, 2004, Mass spectrometry sampling under ambient conditions with desorption electrospray ionization, Science, 306:471-473.

Tanaka, 1988, Protein and polymer analyses up to m/z 1000000 by laser ionization time-of-flight mass spectrometry, Rapid Commun. Mass Spectrom., 2:151-153.

Yamashita, 1984, Electrospray Ion Source. Another Variation on the Free-Jet Theme, J. Phys. Chem., 88:4451-4459.

* cited by examiner

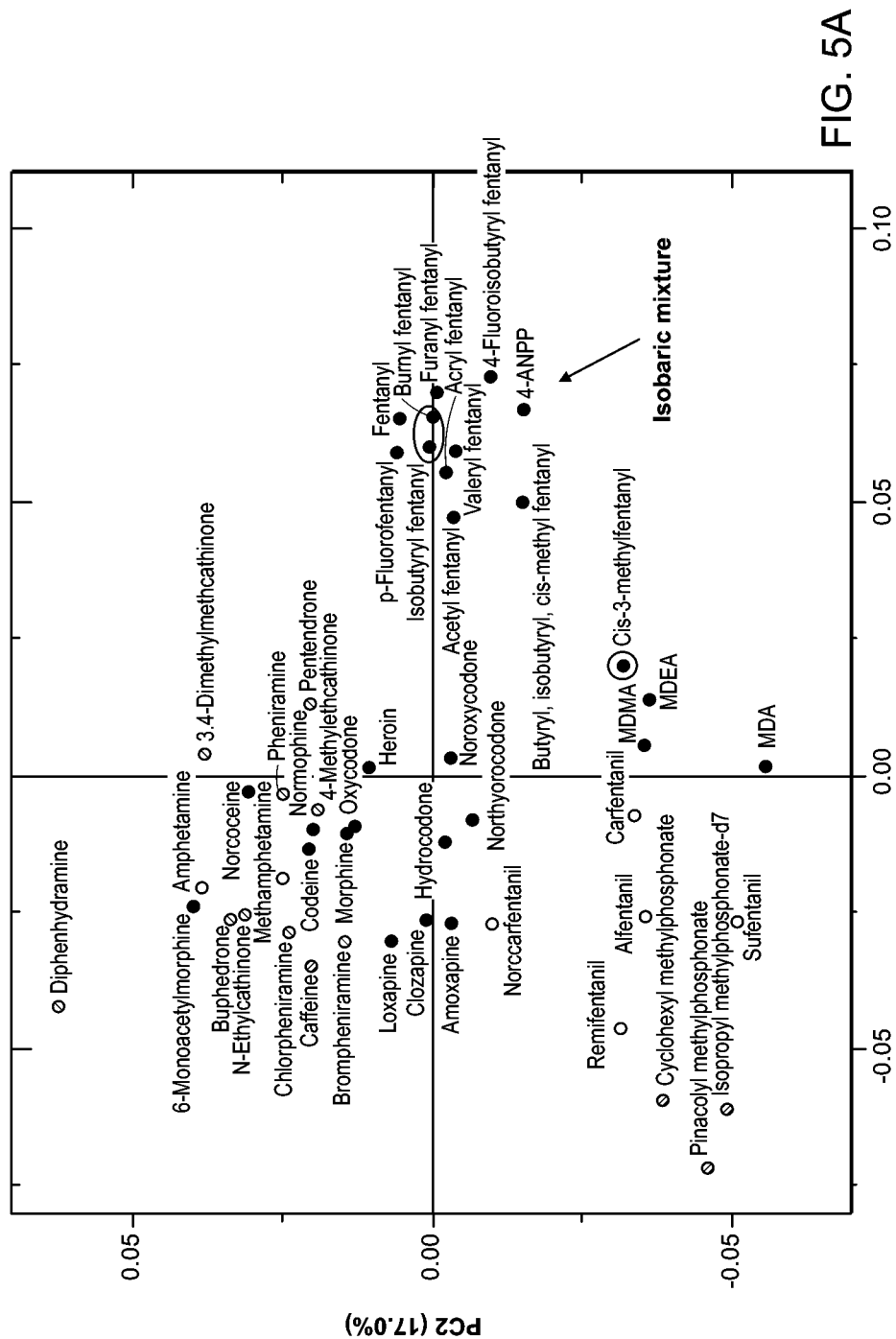

MASS SPECTROMETRY VIA FREQUENCY TAGGING

RELATED APPLICATION

The present application is a 35 U.S.C. § 371 national phase application of PCT/US19/55112, filed Oct. 8, 2019, which claims the benefit of and priority to U.S. provisional application Ser. No. 62/743,600, filed Oct. 10, 2018, the content of each of which is incorporated by reference herein in its entirety.

FIELD OF THE INVENTION

The invention generally relates to mass spectrometry via frequency tagging.

BACKGROUND

Two-dimensional mass spectrometry (2D MS/MS or 2D MS) is a method for correlating precursor ions and product ions without isolation of the former. 2D MS/MS thus allows for the acquisition of the entire 2D MS/MS data domain with a single scan (or pulse sequence in Fourier transform ion cyclotron resonance [FT-ICR] instruments). Its origin can be traced to a 1987 paper by Pfändler et al. in which it was proposed to be useful for studying ion/molecule collisions via a series of rf pulses and delay/reaction times in the cyclotron cell. Subsequently, Guan and Jones described the theory of 2D MS in ICRs and Pfändler provided the first experimental evidence for precursor-product ion correlations using ion/molecule reactions. Other advances include new pulse sequences using stored waveform inverse Fourier transform (SWIFT) for ion radius modulation and denoising algorithms for data analysis. More recently van Agthoven and coworkers have proposed an optimized pulse sequence in which two encoding pulses with optimized voltage amplitudes are separated by a delay time, and after the second pulse the ion signal is observed during the detection period. In addition, others have demonstrated increased precursor ion resolution using nonuniform sampling. Usually infrared multiphoton dissociation is used for fragmentation but several implementations have used electron capture dissociation. After decades of development, 2D MS in FT-ICRs is finding extensive use in applications for analysis of small molecule biologics (cholesterol), peptides and glycopeptides, proteins, and polymers.

SUMMARY

The invention provides systems and methods for correlating precursor and product ion mass-to-charge (m/z) values, without prior isolation, for the linear quadrupole ion trap. Precursor ions are mass-selectively excited using a nonlinear AC frequency sweep at constant RF voltage while, simultaneously, all possible product ions of the excited precursor ions are ejected from the ion trap using a time-varying broadband waveform. The fragmentation time of the precursor ions correlates with the ejection time of the product ions, allowing the time axis to be correlated to precursor ion mass-to-charge. Additionally, product ions' m/z values are encoded by a second induced frequency (the first being the ion's secular frequency) formed from the uneven spacing of the frequency components of the broadband ejection waveform. That is, the product ion m/z values are encoded by unique beat frequencies in the sum of sines and hence they are frequency tagged ions. The invention demonstrate the utility of this method for analyzing structurally related precursor ions, including chemical warfare agent simulants, fentanyls and other opioids, amphetamines, cathinones, antihistamines, and tetracyclic antidepressants. Remarkably, some isobars with similar fragmentation patterns (e.g. cathinones) are readily discriminated from each other without performing a discrete product ion scan.

In certain aspects, the invention provides systems including a mass spectrometer comprising a single ion trap, and a central processing unit (CPU), and storage coupled to the CPU for storing instructions. The instructions, when executed by the CPU cause the system to apply a plurality of scan functions to the single ion trap to fragment a precursor ion and simultaneously eject a product ion of the precursor ion in a manner that preserves in time a relationship of the precursor ion and the product ion.

In other aspects, the invention provides a method for analyzing a sample, that involves introducing a precursor ion of a sample into a mass spectrometer comprising a single ion trap, and analyzing the sample via the mass spectrometer that applies a plurality of scan functions to the single ion trap to fragment the precursor ion and simultaneously eject a product ion of the precursor ion in a manner that preserves in time a relationship of the precursor ion and the product ion.

In certain embodiments of the systems and methods, a value of a mass to charge ratio (m/z) of the precursor ion is directly correlated to fragmentation time. In other embodiments of the systems and methods, the product ion of the precursor ion is ejected by a scan function that comprises a broadband sum of sines. For example the broadband sum of sines comprises nonlinearly spaced frequencies that product unique beats in a waveform that affect ejection and thus modulate spectral peak shapes. The beat frequencies may have a pre-programmed and calibrated relationship with ion secular frequency and hence product ion mass-to-charge. A value of a mass to charge ratio (m/z) of the product ion may be generated by applying a Fourier transform of each mass spectral peak and then converting from beat frequency to product ion m/z. In certain embodiments of the systems and methods, an ionization source that allows for high energy ionization of a sample to generate the precursor ion.

In other embodiments of the systems and methods, a secular or related frequency of the product ion is directly measured by a detector of the mass spectrometer.

In other aspects, the invention provides a mass spectrometer comprising a single ion trap, and a central processing unit (CPU), and storage coupled to the CPU for storing instructions. The instructions, when executed by the CPU cause the system to apply a plurality of scan functions to the single ion trap to excite a precursor and eject a product ion exactly when the precursor is fragmented.

BRIEF DESCRIPTION OF THE DRAWINGS

(FIG. 1A) Precursor ions are fragmented from low to high m/z via a frequency sweep ('Excitation Voltage'), forming product ions. Each product ion is 'tagged' with a secondary frequency by resonance excitation with two frequencies close to its secular frequency, the difference of which creates a beat frequency that modulates the mass spectral peak shapes. When product ions are generated they are immediately ejected and detected by a broadband sum of sines with encoded beat frequencies, but the ejection process follows the programmed beat pattern and hence the mass spectral peaks also show beats. (FIG.

1B) The beat frequencies, related linearly to product ion secular frequency, can be recovered by taking the fast Fourier transform of each peak. The beats can be plotted against the experimental secular frequencies for calibration. (FIG. 1C) Experimental vs. calibrated relationship between beat frequency and product ion m/z in 'high mass' mode (LMCO ~100 Th) on the LTQ.

(FIG. 3A) Full scan mass spectrum of the mixture (note the beats in the spectra), (FIG. 3B) beat frequency spectra for each precursor ion, (FIG. 3C) comparison of frequency spectra of three isobaric fentanyls and three-component mixture. Known product ions are marked. Data was acquired in 'high mass' mode.

FIG. 5A shows principal component analysis of all frequency spectra acquired on the LTQ (with isobars circled in red and isobaric mixture noted).

DETAILED DESCRIPTION

The invention provides frequency tagging methods for 2D MS on quadrupole ion traps using simple collision-induced dissociation for precursor ion fragmentation and show experimental evidence that precursor and product ion m/z values can both be obtained—and correlated—in a single scan. Herein, a nonlinear frequency sweep is used for time-dependent fragmentation of precursor ions from low to high m/z in one dimension of the linear trap and eject all product ions of those precursor ions as they are being formed by using a broadband sum of sines waveform applied in the orthogonal dimension. The sum of sines is encoded with beat frequencies proportional to the product ion secular frequencies, thus modulating peak shapes according to those beat frequencies. By taking the fast Fourier transform of each peak, the beat frequencies of the ejected product ions—hence, the product ions' secular frequencies—can be recovered for every precursor ion without isolation. Secular frequency can then be converted to ion m/z, and subsequently product ion frequency spectra can be converted to the mass domain, thereby yielding a product ion spectrum for every precursor ion.

Figure 1A:
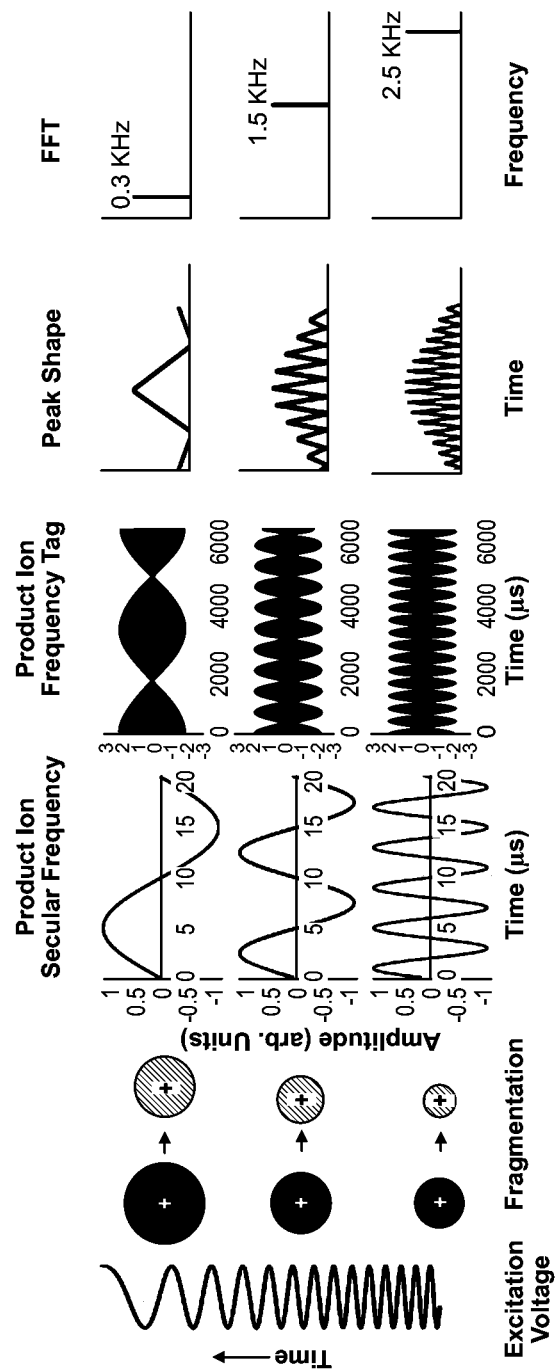
FIGS. 1A-C show frequency tagging mass spectrometry for 2D MS/MS.

Frequency tagging (FIG. 1A) is a method of tagging ions resonantly ejected from a quadrupole ion trap with a secondary frequency observable at the detector, the primary frequency being the ion's fundamental secular frequency which is usually not observed except when measuring charge induction current in the ion trap. Any ion in the trap can be frequency tagged by applying a dual frequency sine wave that is the sum of the ion's secular frequency and a second frequency very close to the secular frequency. For example, an ion whose secular frequency is 300 kHz can be tagged with a 2 kHz frequency if a dual frequency sine wave containing 300 kHz and 302 kHz is used for resonance ejection (or excitation). The 2 kHz beat is observed in the mass spectral peak at the detector (FIG. 1A, peak shape). The peak can be the result of a precursor ion scan, a neutral loss scan, or a full scan. A fast Fourier transform of the mass spectral peak results in recovery of the beat frequency, and if beat frequency and the secular frequency are related in some predetermined or pre-programmed (but calibratable) fashion, then this relationship can be used to relate beat frequency to product ion m/z.

Figure 1B:
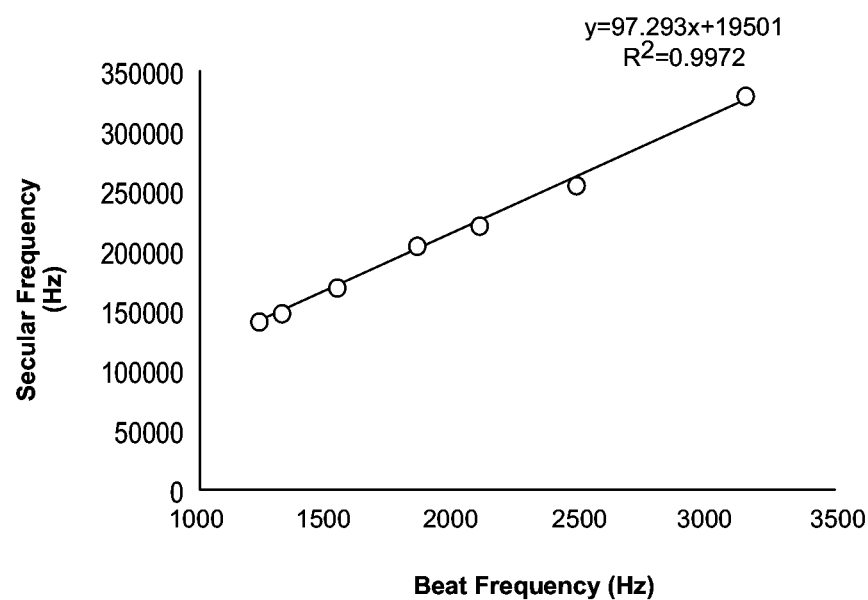

Herein, frequency tagging was used to perform 2D MS/MS in a linear quadrupole ion trap. There are three key pieces of information obtained in a 2D MS/MS experiment: 1) precursor ion m/z, 2) product ion m/z, and 3) the relationship between the precursor ions and the product ions (i.e. from which precursor ion did each product ion originate?). In our implementation of 2D MS/MS, these three pieces of information are obtained as follows. 1) Precursor ion m/z is linearly related to time because the precursor ions are fragmented from low to high m/z using an inverse Mathieu q scan ('Excitation Voltage vs. Time' in FIGS. 1A-C). 2) Simultaneously, a broadband sum of sines waveform—with encoded beat frequencies—is used to eject the product ions as they are being formed from fragmentation of the precursors. Product ion m/z is recovered from fast Fourier transform of each mass spectral peak, where beat frequency is linearly related to secular frequency based on a pre-programmed relationship (which is then directly correlated to product ion m/z). FIG. 1B shows the experimentally observed relationship between secular frequency and beat frequency, and converting secular frequency to m/z gives the plot in FIG. 1C. The calibration is shown in blue and the experimental values in red. 3) Product ions are ejected from the ion trap at the same time as their respective precursor ions are fragmented and hence their relationship is preserved in time, as was the case in our implementation of precursor and neutral loss scans.[23-26,37] The application of two waveforms, an inverse Mathieu q scan for precursor ion fragmentation and a broadband beat-encoded sum of sines for product ion ejection, thus allows us to obtain the entire MS/MS domain with one scan.

2D MS/MS Using Frequency Tagging

Figure 2A:
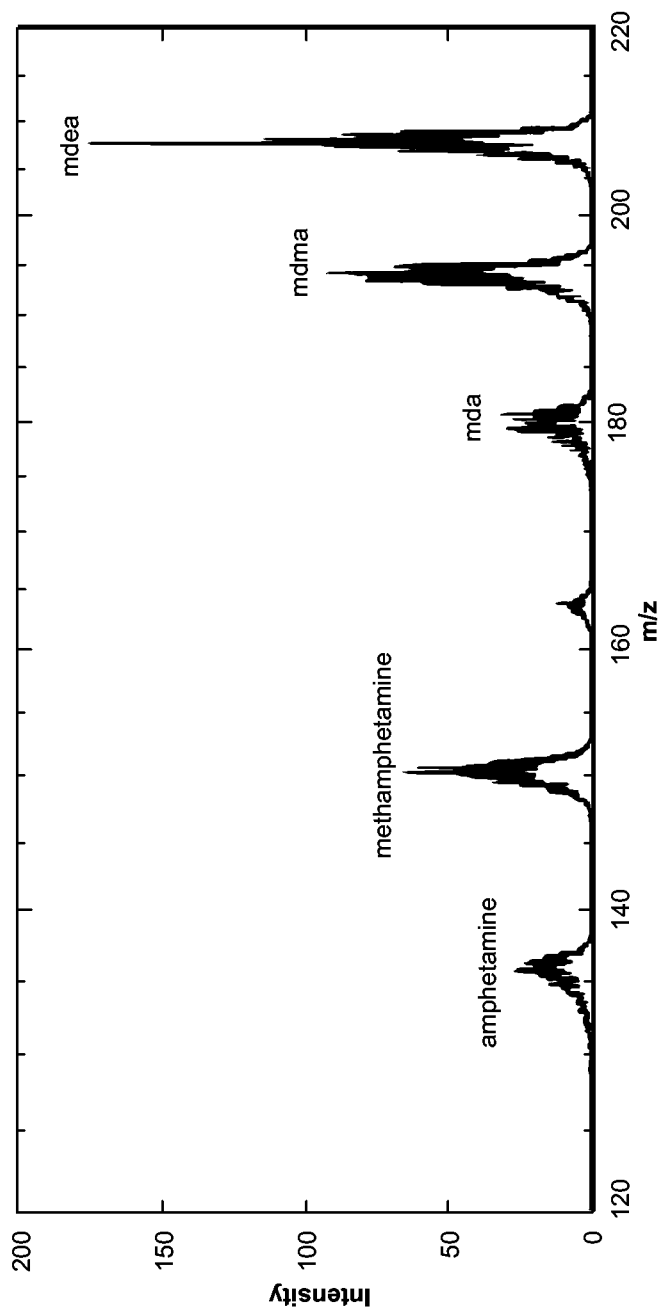
FIG. 2A shows frequency tagging mass spectrum in 'low mass' mode on the LTQ for five amphetamines (note the beats in each peak) and FIG. 2B shows frequency spectrum of each peak. Frequencies that correspond to known product ions are marked.

A simple mixture of 5 amphetamines was analyzed using this 2D MS/MS method. The mass calibrated spectrum in FIG. 2A gives the m/z values of the precursor ions as a function of time, thus satisfying requirement #1 of 2D MS/MS. Note the unique beats in each peak which will be used to recover product ion m/z. It is also critical to remember that although the precursor ion m/z correlates with time, the precursor ions are never detected. Only the product ions are observed at the detector.

Requirement #3, association between fragmented precursor ion m/z and generated product ion m/z, is satisfied by taking the fast Fourier transform of any given peak in the spectrum. Because we know that each peak is due only to one precursor ion, we can be sure that any peaks in the fast Fourier transform of the mass peak are product ions formed from fragmentation of the selected precursor ion. Of course, this does not hold if there is substantial overlap or if there are isobars (in that case the FFT will give peaks from both precursors, as shown below).

Figure 1C:
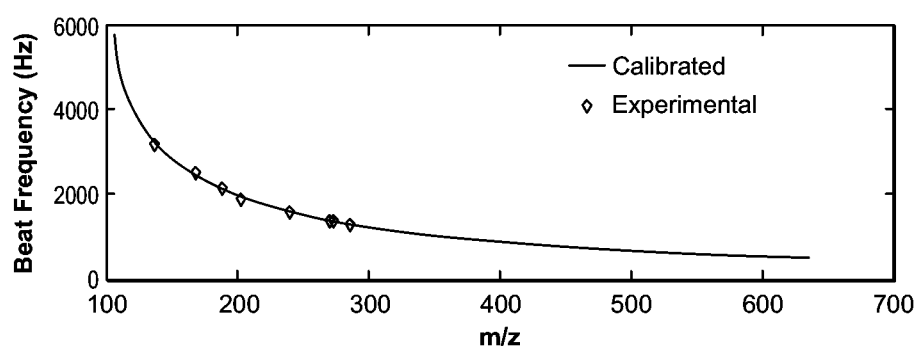

In order to obtain the product ion m/z (requirement #2), it is important to associate the peaks in the beat frequency domain (after FFT) with particular m/z values. Experimentally this can be done by taking FFTs of peaks of known standards and correlating beat frequency with the known product ion m/z. Because in our case beat frequency and secular frequency are directly proportional, we can calculate the calibrated relationship between beat frequency and m/z, as shown in FIG. 1C and compare it to experimental values, shown as red diamonds. These calibrations can now be used to confidently assign m/z values in the frequency spectra. Note that the calibration shown is only applicable to 'high mass' mode. In low mass' mode the rf voltage is lower and thus the relationship between m/z and secular frequency (and beat frequency) is different.

Figure 2B:
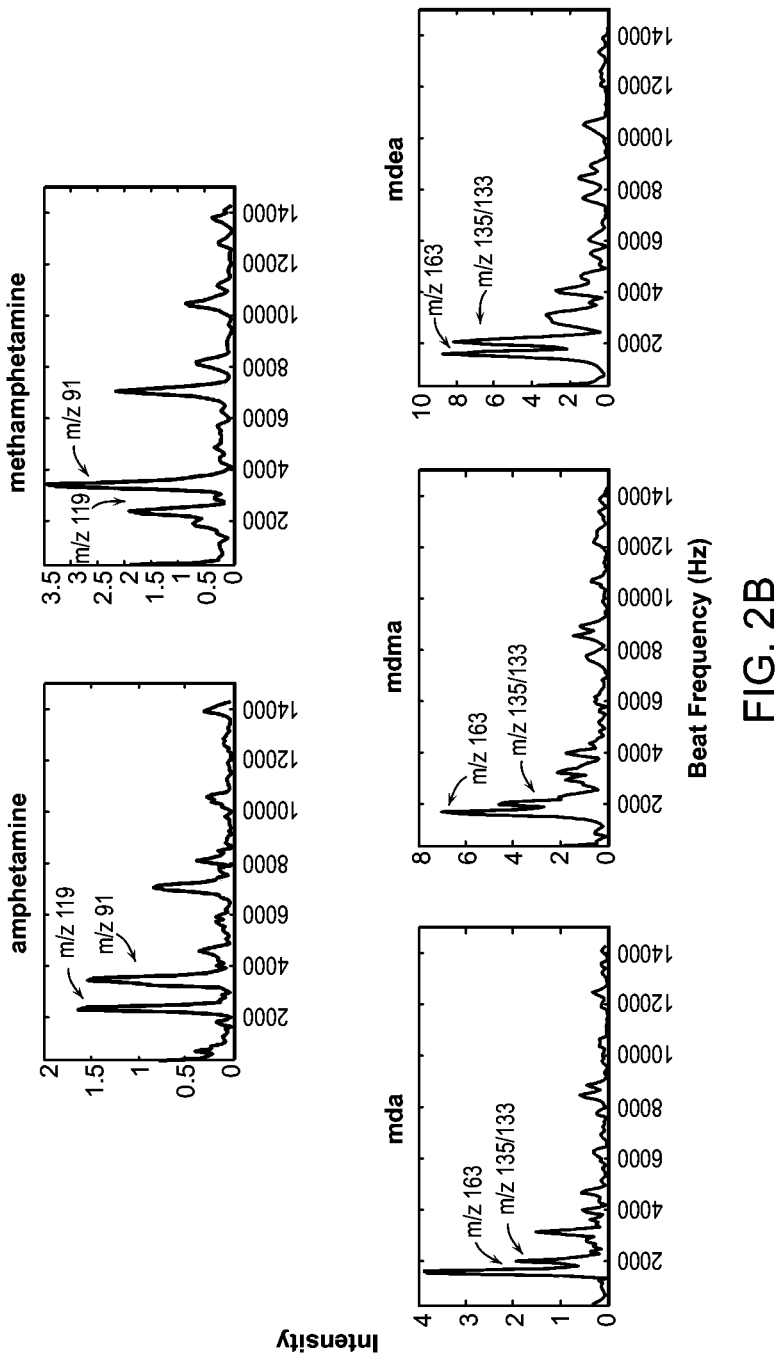

Amphetamine and methamphetamine share product ions at m/z 91 and 119, and this is evident in the FFTs (FIG. 2B) of the peaks in the mass spectrum (FIG. 2A). A peak at 3436 Hz corresponds to m/z 91 and 2386 Hz corresponds to m/z 119. Because beat and secular frequency are proportional in our implementation, lower m/z ions will have higher beat frequencies. Similarly, amphetamines mda, mdma, and mdea fragment to m/z 163, m/z 135, and m/z 133 at 1527 Hz and 2005 Hz, respectively. Additional peaks in the frequency spectra correspond to harmonics (i.e. two and three times the beat frequency) as well as other, less predictable beats and combination frequencies. Because of these additional peaks, frequency spectra are not converted into the mass domain. However, these peaks do serve to provide a unique pattern for each precursor ion and may be useful for distinguishing similar spectra.

2D MS/MS for Analysis of Fentanyls

Figure 3A:
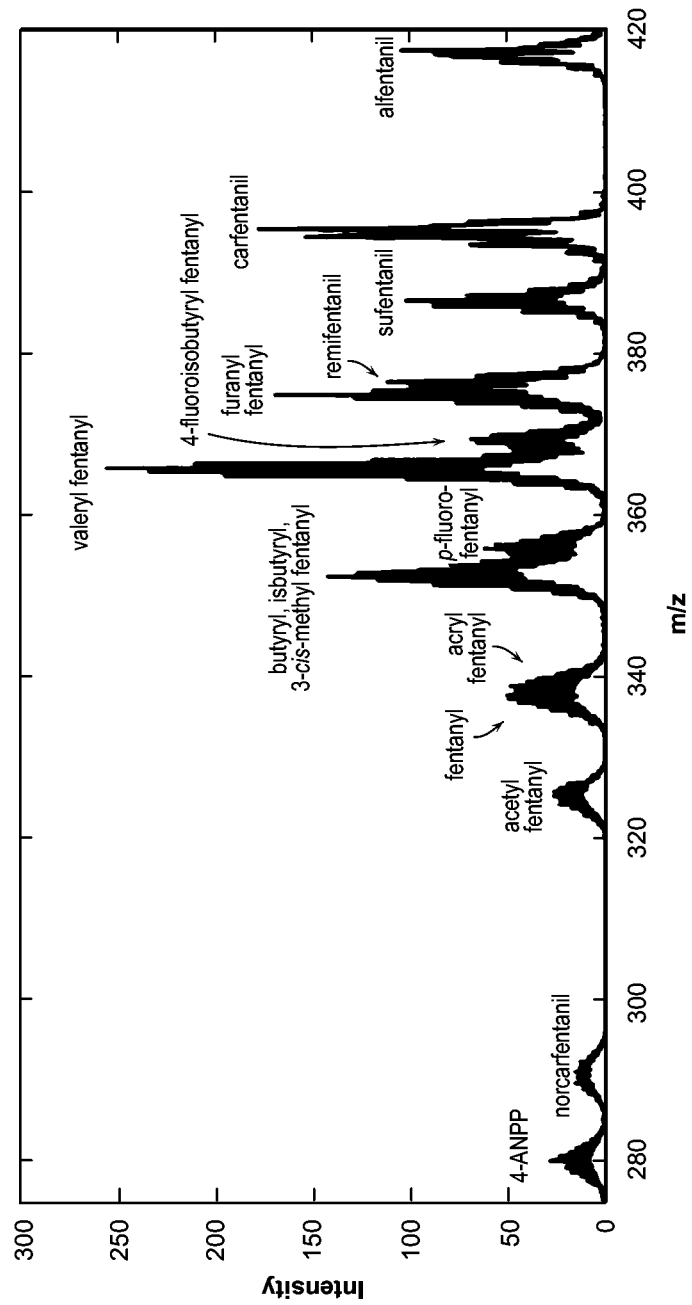
FIGS. 3A-C show 2D MS/MS of a mixture of 16 fentanyl analogues.
Figure 3B:
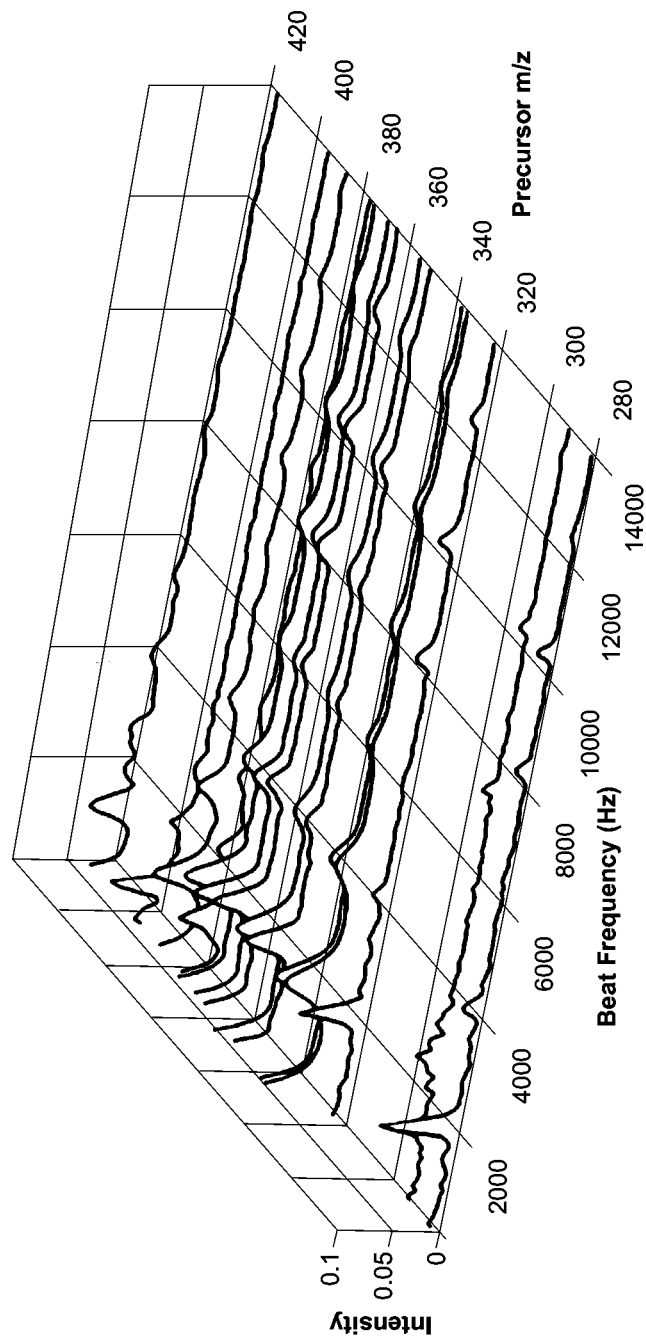
Figure 4:
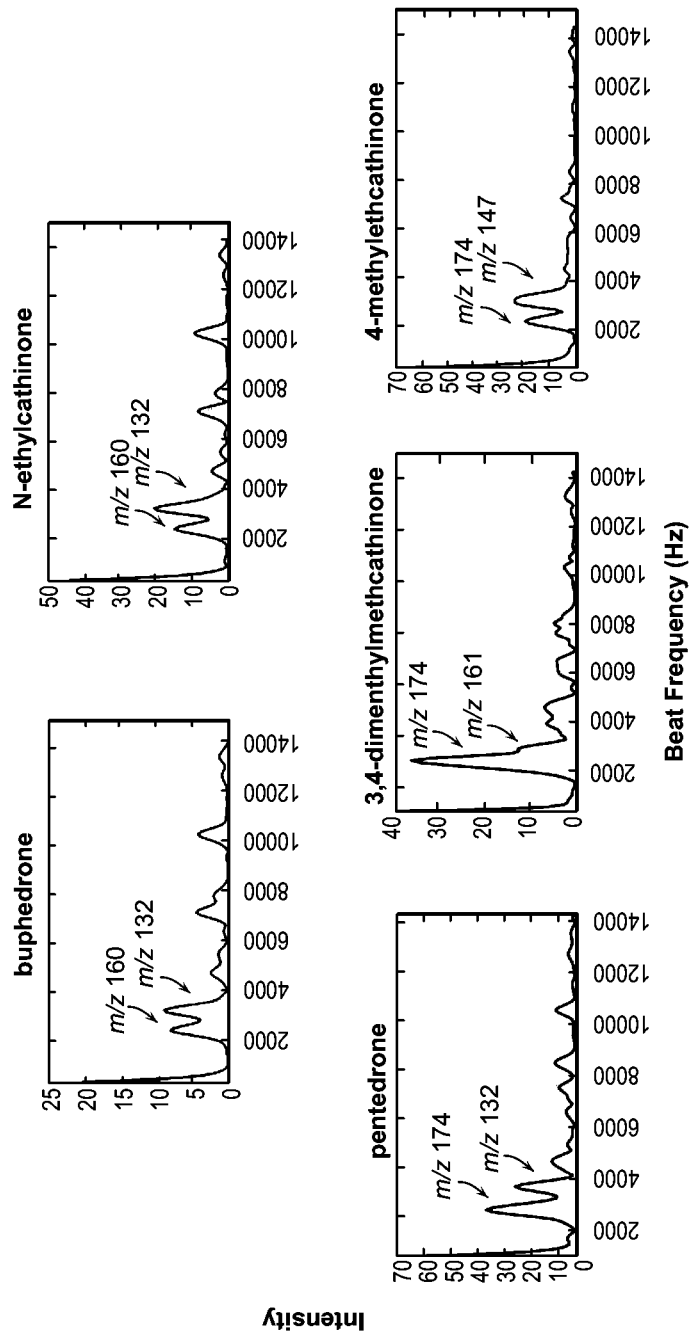
FIG. 4 shows frequency spectra of sets of cathinone isobars: m/z 178 isobars buphedrone and N-ethylcathinone; m/z 192 isobars pentedrone, 3,4-dimethylcathinone, and 4-methylethcathinone. Data was acquired in 'high mass' mode.

2D MS/MS was next applied to analysis of opioids of the fentanyl class, which have become a serious health risk due to their extreme potency and wide range of analogues.[38,39] When subject to CID in the ion trap, many of these compounds fragment almost exclusively to m/z 188[40] and so their frequency spectra should be markedly similar. A full scan of a mixture of 16 fentanyl analogues appears in FIG. 3A. The precursor ion masses are directly proportional to time, allowing for the spectrum to be mass calibrated. The beats in each peak are indicative of the product ion m/z values and be recovered through FFTs. As shown in FIG. 3B, 4-ANPP (a fentanyl precursor), acetyl fentanyl, 4-fluoroisobutyryl fentanyl, fentanyl, furanyl fentanyl, p-fluorofentanyl, isobutyryl fentanyl, butyryl fentanyl, valeryl fentanyl, and acryl fentanyl all fragment to m/z 188 and hence have almost identical frequency spectra. Cis-3-methylfentanyl has a prominent product ion at m/z 202 which is noticeably frequency shifted (about 240 Hz) from m/z 188. Acetyl norfentanyl is a metabolite and hence fragments differently as well.

Figure 3C:
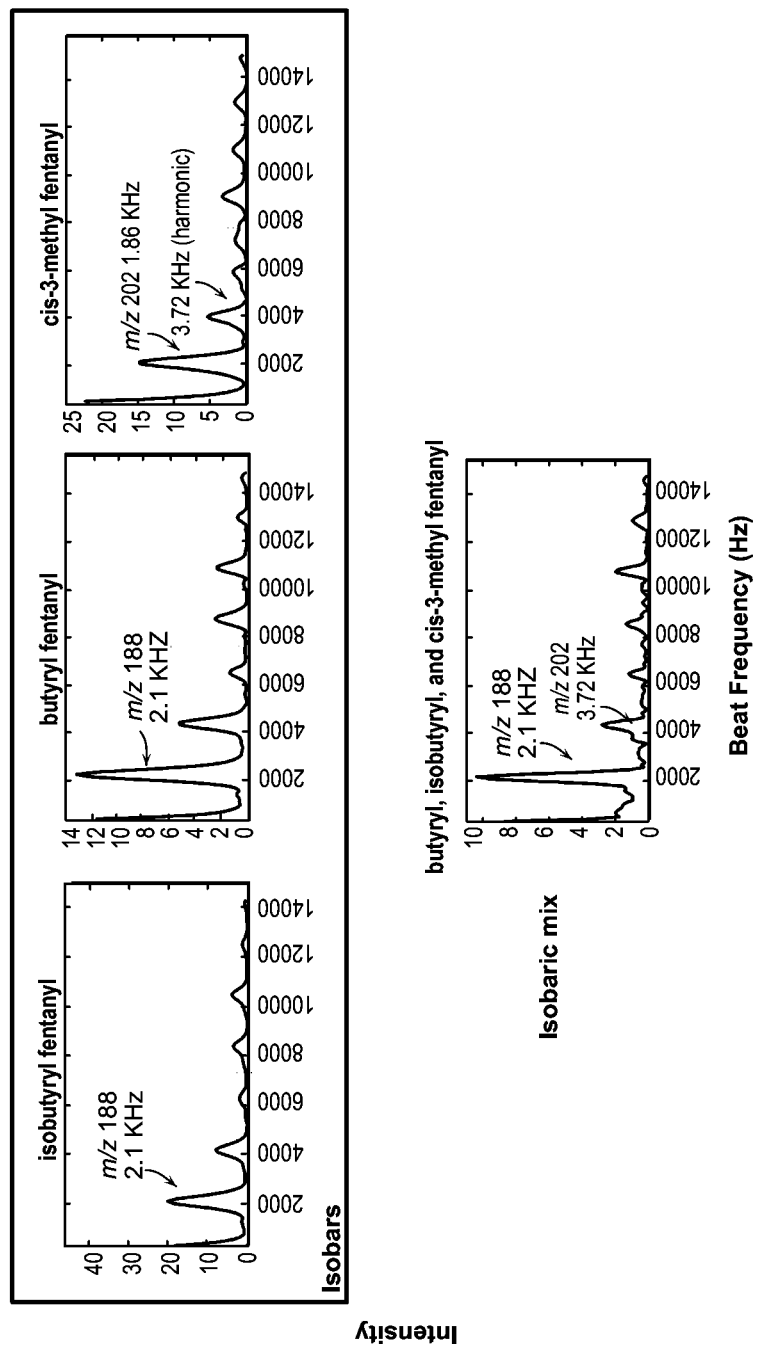

Notably, butyryl, isobutyryl, and cis-3-methylfentanyl are isobaric (m/z 351) and so their peaks overlap in the mass spectrum if they are in a mixture together. We tested whether we could observe all three components in a 1:1:1 mixture. The frequency spectrum in FIG. 3C (bottom) indicates a primary product ion at m/z 188. Presumably the peak at m/z 202 overlaps significantly and is not observed. However, the harmonic (1.86 kHz×2=3.72 kHz) is observed because it is twice as far from the harmonic of m/z 188 compared to the fundamental frequencies, and thus it is umambiguous that methylated fentanyl is in the spectrum. Later we will give statistical evidence that all three components are evident in the frequency spectrum. Butyryl and isobutyryl fentanyl are nearly indistinguishable, though.

Figure 7:
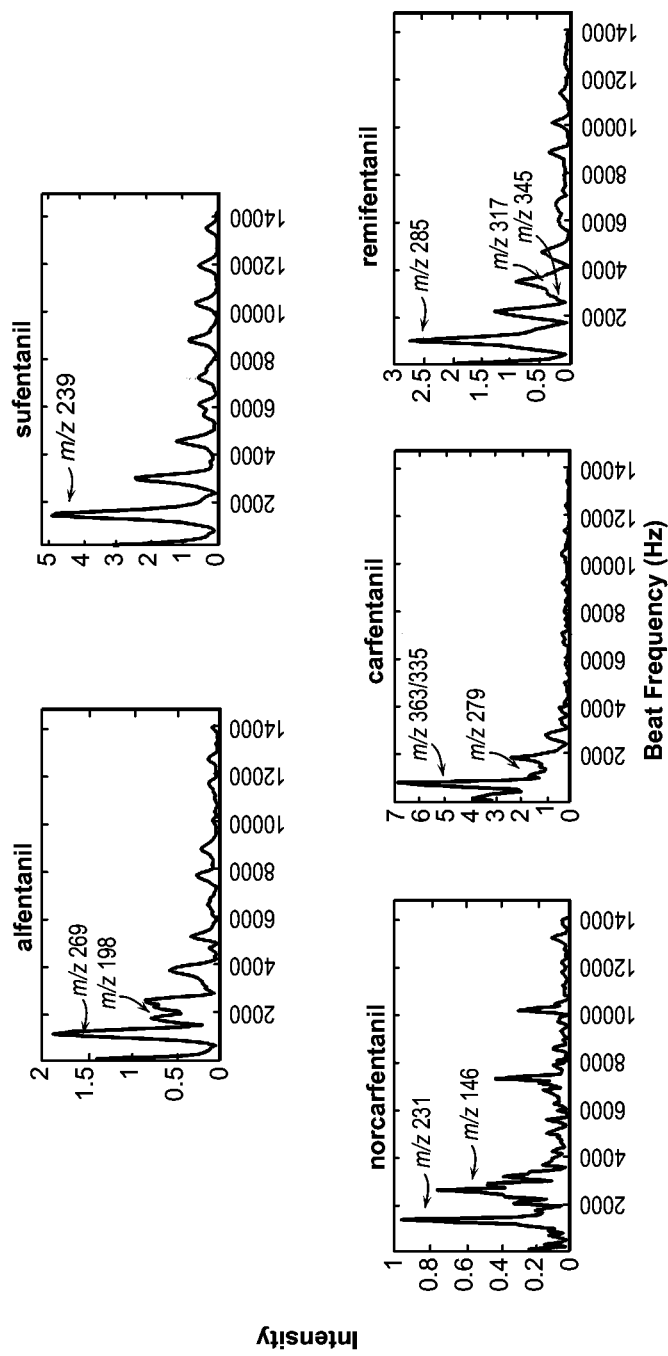
FIG. 7 shows frequency tagging spectra of five fentanils in 'high mass' mode.

Quaternary fentanils (emphasis on the 'il') share neutral losses—e.g. 31 Da, 32 Da, 60 Da, 148 Da are examples—instead of product ions. In the frequency domain the similarities are not obvious, which is a weakness of the current method. The frequency domain must be converted to the mass-to-charge domain and then to neutral losses to make any reasonable conclusions about similarities between spectra. FIG. 7 shows the frequency spectra of alfentanil and sufentanil (which share neutral losses of 31 Da and 148/149 Da) and norcarfentanil, carfentanil, remifentanil (which share neutral losses of 32 Da, 60 Da, and 149 Da).

2D MS/MS for Analysis of Other Molecular Classes

Figure 8:
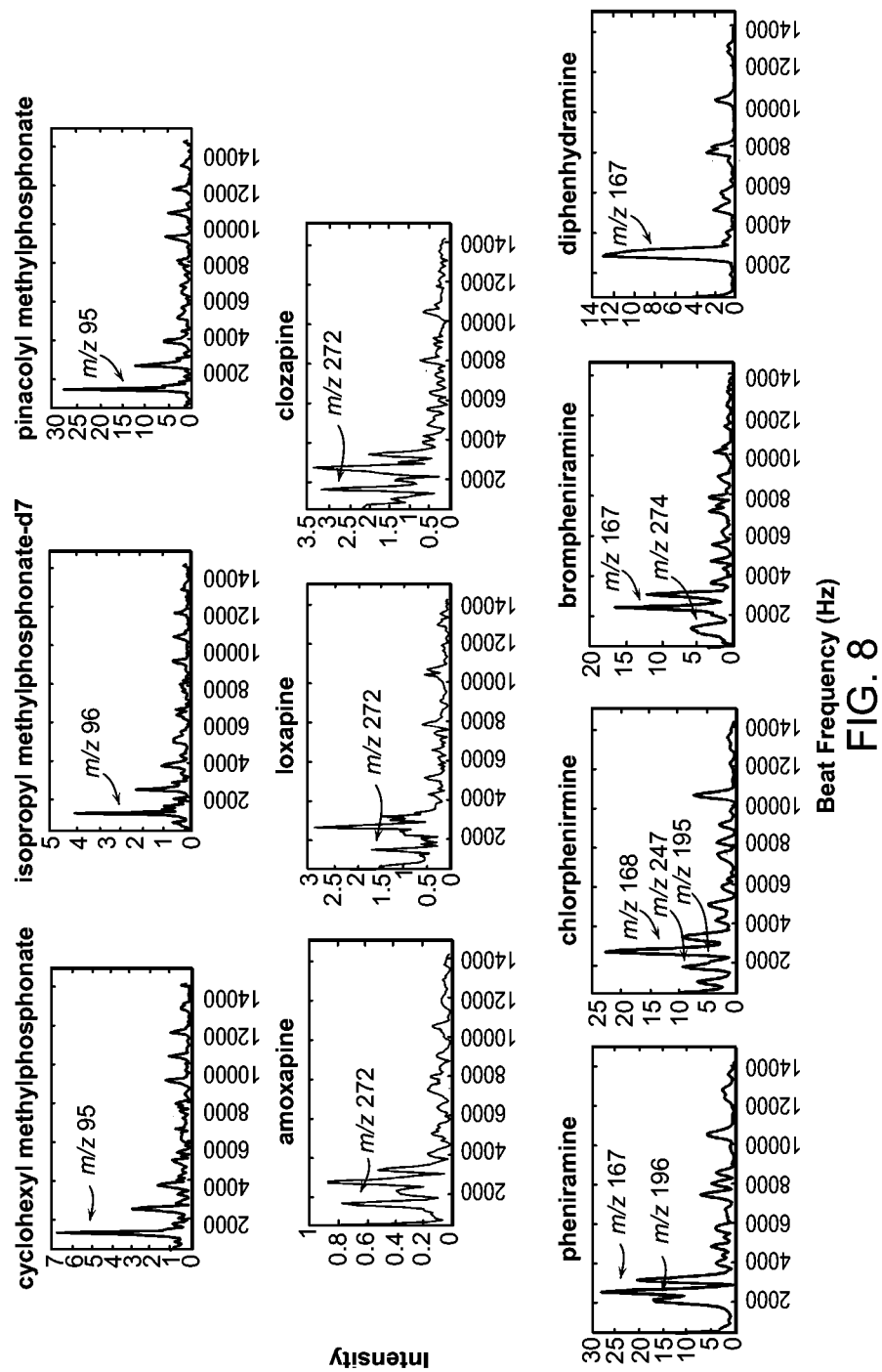
FIG. 8 shows frequency tagging spectra for (top, green) three chemical warfare agent simulants, (middle, dark blue) three tetracyclic antidepressants, and (bottom, red) four antihistamines. The chemical warfare agent spectra were obtained at a LMCO of 65 Th; other data was obtained in 'high mass' mode (LMCO 100 Th).
Figure 9:
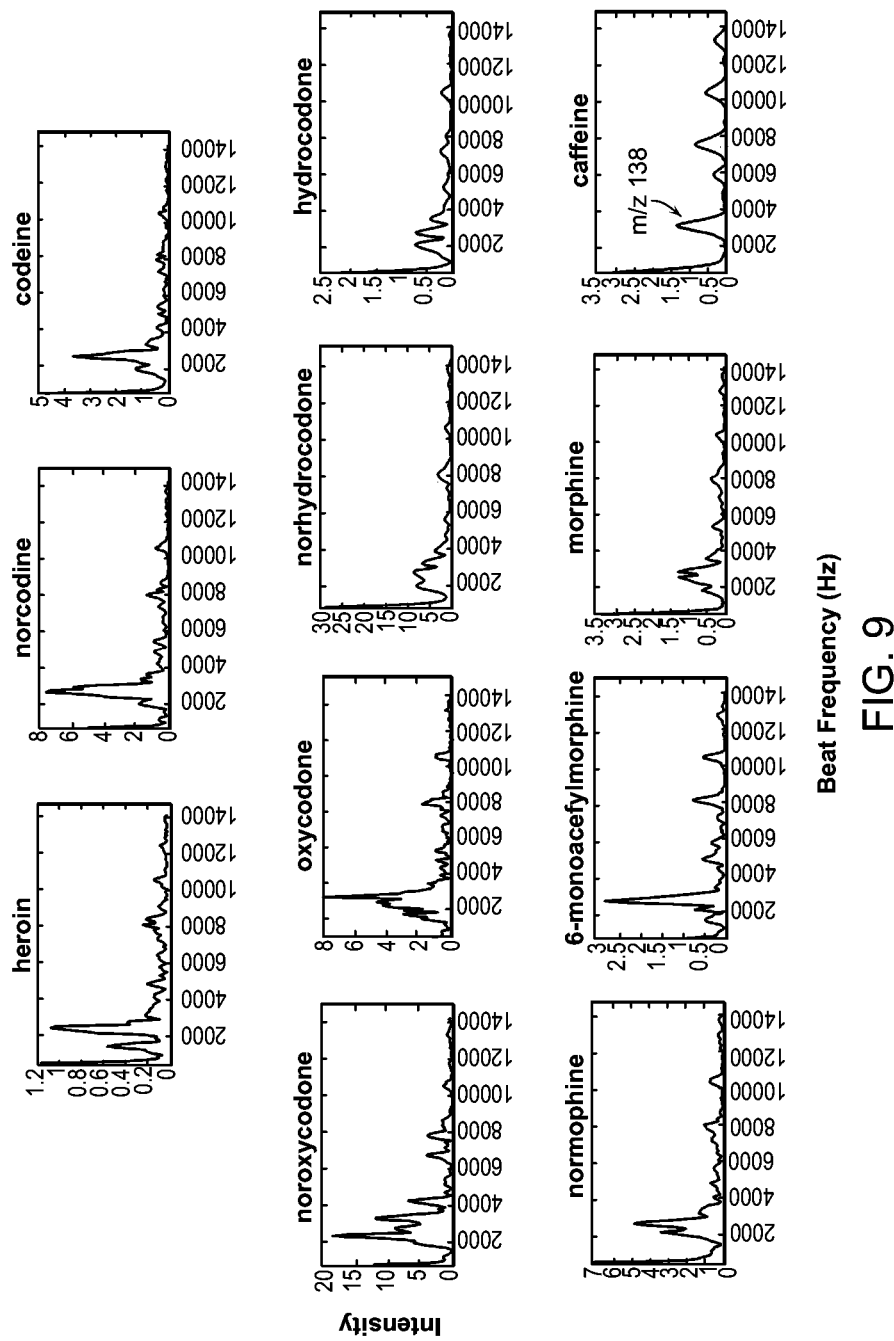
FIG. 9 shows frequency tagging spectra of opioid standards and metabolites as well as caffeine. All data was acquired in 'high mass' mode.

Frequency tagging spectra of other molecular classes—focusing on classes that share product ions rather than neutral losses—are shown in FIGS. 8-9. Chemical warfare agent simulants cyclohexyl methylphosphonate, isopropyl methylphosphonate-d7, and pinacolyl methylphosphonate fragment exclusively to m/z 95 (m/z 96 for the deuterated analytes) in the negative ion mode and thus have very similar frequency spectra, including strong harmonics. Tetracyclic antidepressants amoxapine, loxapine, and clozapine share m/z 272 but otherwise have dissimilar spectra in both the mass and frequency domain. Antihistamines pheniramine, chlorpheniramine, brompheniramine, and diphenhydramine share m/z 167 (or m/z 168), as noted on the spectra, but also have other dissimilar product ions. Other opioids (along with caffeine as a reference spectrum) were analyzed, with results in FIG. 9. These spectra were more difficult to deconvolute and are not labeled but will be statistically analyzed later.

Analysis of Isobaric Cathinones

A challenge in mass spectrometry is differentiating isobars, particularly if those isobars fragment similarly. Not only will their product ion spectra appear similar, but so will their 2D MS/MS frequency spectra. As shown in FIG. 4, isobaric cathinones (m/z 178) buphedrone and N-ethylcathinone share product ions at m/z 160 and 132 and are nearly indistinguishable. However, three other cathinone isobars, namely pentedrone, 3,4-dimethylmethcathinone, and 4-methylethcathinone are—remarkably—readily distinguished. Although they share water loss (m/z 174), they also have unique $MS^2$ ions m/z 132, m/z 161, and m/z 147. As we showed previously, mixtures of isobars can also be identified if standard spectra of the individual components are known.

Statistical Analysis of Beat Frequency Spectra

Figure 5B:
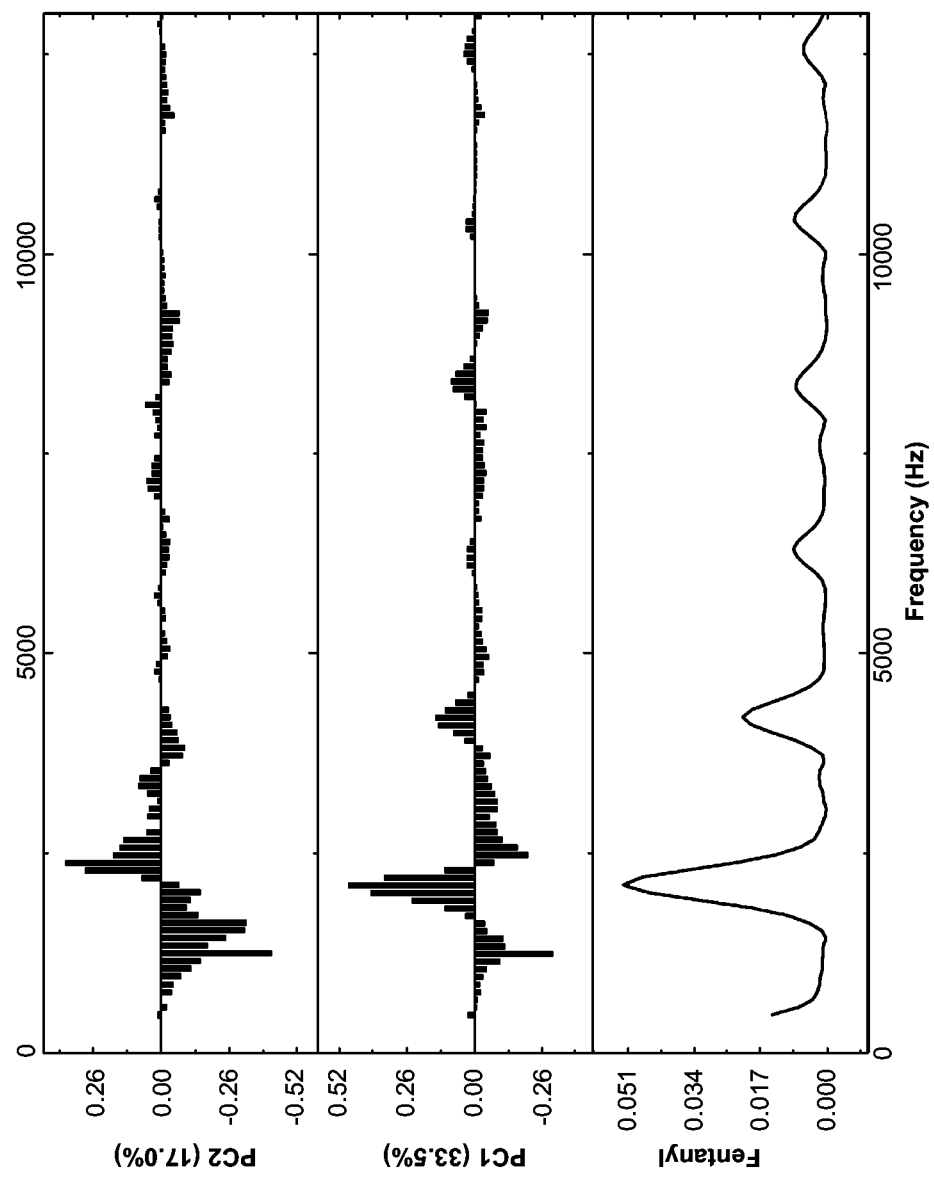
FIG. 5B shows loadings for each frequency with fentanyl FFT as the reference.

After acquiring frequency spectra for 47 compounds of various molecular classes and normalizing the integrated intensity of each spectrum to 1, we performed principal component analysis to statistically distinguish molecular classes. FIG. 5A shows the PCA plot with each molecular class color coded with the same color as their frequency spectra. Clearly the fentanyls group together because of their strong similarities as well as methylphosphonates (chemical warfare agent simulants), and methylenedioxyamphetamines. Tetracyclic antidepressants clozapine, loxapine, and amoxapine also group closely together, and isobars buphedrone and N-ethylcathinone are close. Fentanils are scattered because they have neutral losses in common instead of a fixed product ion m/z and this particular analysis will group based on shared product ions. Other opioids, cathinones, and antihistamines do not separate well because they have more complex fragmentation patterns and because the frequency resolution—hence mass resolution—of the product ions is quite low. FIG. 5B shows loading plots and the fentanyl frequency spectrum for reference. Clearly, m/z 188 is the strongest contributor to principal component 1 and thus gives good separation between fentanyls and other classes. Principal component 2 focuses on higher mass peaks than m/z 188 (lower frequencies) and provides better separation amongst some of the other classes.

The three points circled in red are isobaric fentanyls (m/z 351). Isobutyryl and butyryl fentanyl have nearly identical product ion spectra (product ion m/z 188) which is evident in their frequency spectra and in the PCA plot, and cis-3-methylfentanyl fragments instead to m/z 202 and thus falls in an entirely different location. An isobaric mixture of 1:1:1 isobutyryl:butyryl:cis-3-methyl fentanyl was analyzed by frequency tagging and it appropriately lies between the circled individual components on the PCA plot.

Software Ion Scan Functions of 2D MS/MS Data

Figure 6:
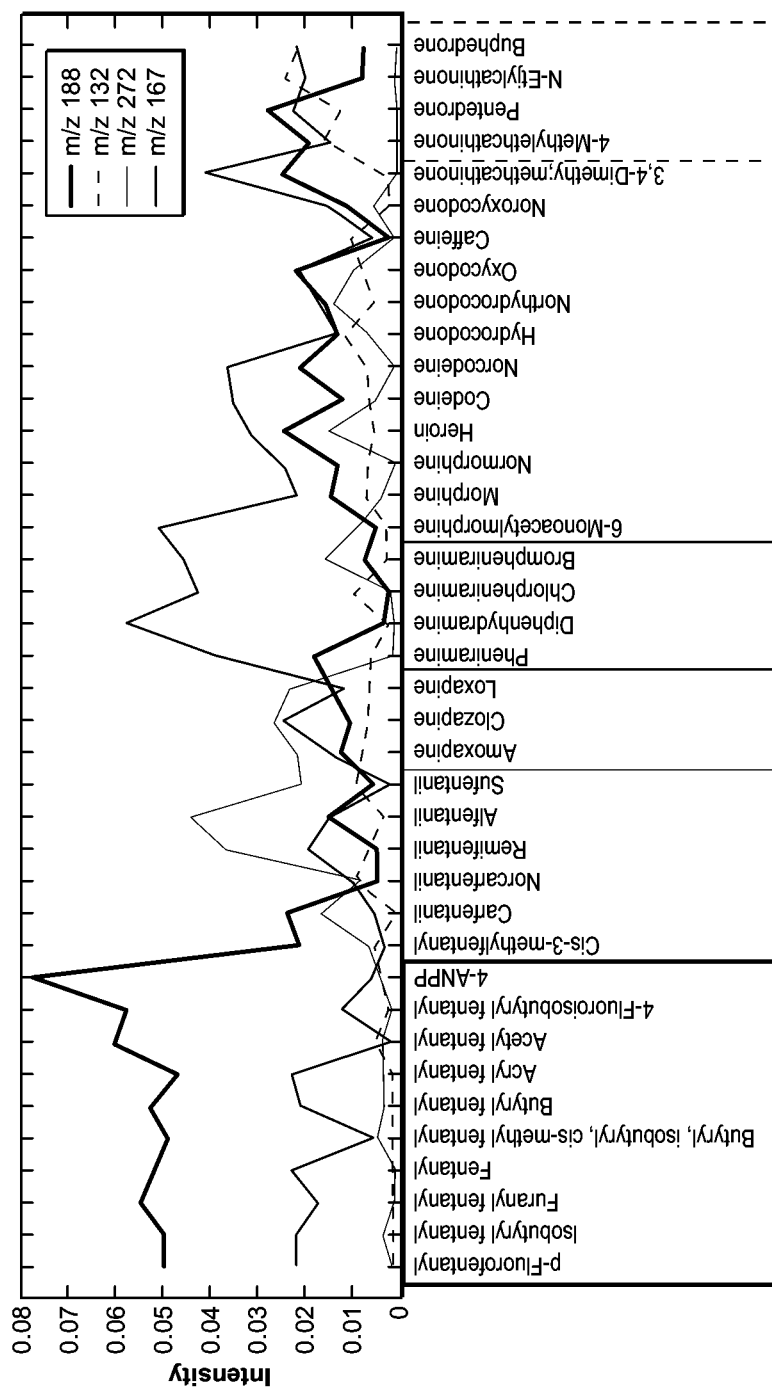
FIG. 6 shows reconstructed software precursor ion scans for selected product ions.

Principal component analysis is only one way to analyze the frequency tagging data and furthermore is not necessarily the best method of analysis. We can also reconstruct precursor ion 'spectra' from the recorded frequency spectra, i.e. perform 'software ion scans'. For example, a reconstructed precursor scan of m/z 188 (FIG. 6, blue) yields the fentanyls as the most abundant analytes. A software precursor scan of m/z 132 yields three of the cathinones, a precursor scan of m/z 272 yields the tetracyclic antidepressants amoxapine, clozapine, and loxapine (as well as some fentanils which have very broad peaks in their frequency spectra), and a reconstructed precursor scan of m/z 167 shows the pheniramines as prominent ions with that functionality. The low frequency and mass resolution of the product ions does mean that there is substantial overlap in the spectra, and improvements to the resolution should be the next major step in this work. Note that the amphetamines and CWAs were analyzed at different rf amplitudes and were not included in these reconstructed spectra.

Other Methods of Analysis

This 2D MS/MS method may be used in conjunction with a database of frequency spectra. Known standards would be analyzed using a given waveform and the frequency spectra would be stored for comparison with unknown samples. A portable mass spectrometer would especially benefit from this technology since many are notoriously slow (1 Hz acquisition rate for systems with a discontinuous atmospheric pressure interface). The ability to acquire more information than could be obtained in any other scan mode (full scan, product scan, precursor scan, and neutral loss scan) could improve the efficiency of sample analysis for these systems. Of course, the product ion resolution is quite low, and so product ion scans should always be used to confirm the identity of unknowns.

Inverse Mathieu q Scan

An inverse Mathieu q scan is described in U.S. application Ser. No. 15/789,688, the content of which is incorporated by reference herein in its entirety. An inverse Mathieu q scan operates using a method of secular frequency scanning in which mass-to-charge is linear with time. This approach contrasts with linear frequency sweeping that requires a complex nonlinear mass calibration procedure. In the current approach, mass scans are forced to be linear with time by scanning the frequency of a supplementary alternating current (supplementary AC) so that there is an inverse relationship between an ejected ion's Mathieu q parameter and time. Excellent mass spectral linearity is observed using the inverse Mathieu q scan. The rf amplitude is shown to control both the scan range and the scan rate, whereas the AC amplitude and scan rate influence the mass resolution. The scan rate depends linearly on the rf amplitude, a unique feature of this scan. Although changes in either rf or AC amplitude affect the positions of peaks in time, they do not change the mass calibration procedure since this only requires a simple linear fit of m/z vs time. The inverse Mathieu q scan offers a significant increase in mass range and power savings while maintaining access to linearity, paving the way for a mass spectrometer based completely on AC waveforms for ion isolation, ion activation, and ion ejection.

Methods of scanning ions out of quadrupole ion traps for external detection are generally derived from the Mathieu parameters $a_u$ and $q_u$, which describe the stability of ions in quadrupolar fields with dimensions u. For the linear ion trap with quadrupole potentials in x and y, $$q_x = -q_y = 8zeV_{0-p}/\Omega^2(x_0^2 + y_0^2)m \quad (1)$$

$$a_x = -a_y = 16zeU/\Omega^2(x_0^2 + y_0^2)m \quad (2)$$

where z is the integer charge of the ion, e is the elementary charge, U is the DC potential between the rods, $V_{0-p}$ is the zero-to-peak amplitude of the quadrupolar radiofrequency (rf) trapping potential, $\Omega$ is the angular rf frequency, $x_0$ and $y_0$ are the half distances between the rods in those respective dimensions, and m is the mass of the ion. When the dimensions in x and y are identical ($x_0 = y_0$), $2r_0^2$ can be substituted for ($x_0^2 + y_0^2$). Solving for m/z, the following is obtained:

$$m/z = 4V_{0-p}/q_x\Omega^2 r_0^2 \quad (3)$$

$$m/z = 8U/a_x\Omega^2 r_0^2 \quad (4)$$

Ion traps are generally operated without DC potentials ($a_u = U = 0$) so that all ions occupy the q axis of the Mathieu stability diagram. In the boundary ejection method, first demonstrated in the 3D trap and in the linear ion trap, the rf amplitude is increased so that ions are ejected when their trajectories become unstable at q=0.908, giving a mass spectrum, i.e. a plot of intensity vs m/z since m/z and rf amplitude (i.e. time) are linearly related.

The basis for an inverse Mathieu q scan is derived from the nature of the Mathieu parameter $q_u$ (eq. 3). In order to scan linearly with m/z at constant rf frequency and amplitude, the $q_u$ value of the m/z value being excited should be scanned inversely with time t so that $$q_u = k/(t-j) \quad (5)$$

where k and j are constants determined from the scan parameters. In the mode of operation demonstrated here, the maximum and minimum $q_u$ values ($q_{max}$ and $q_{min}$), which determine the m/z range in the scan, are specified by the user. Because the inverse function does not intersect the q axis (e.g. $q_u = 1/t$), the parameter j is used for translation so that the first q value is $q_{max}$. This assumes a scan from high q to low q, which will tend to give better resolution and sensitivity due to the ion frequency shifts mentioned above.

The parameters j and k are calculated from the scan parameters, $$j = q_{min}\Delta t/(q_{min} - q_{max}) \quad (6)$$

$$k = -q_{max}j \quad (7)$$

where $\Delta t$ is the scan time. Operation in Mathieu q space gives advantages: 1) the waveform frequencies depend only on the rf frequency, not on the rf amplitude or the size or geometry of the device, which implies that the waveform only has to be recalculated if the rf frequency changes (alternatively, the rf amplitude can compensate for any drift in rf frequency), and 2) the mass range and scan rate are controlled by the rf amplitude, mitigating the need for recalculating the waveform in order to change either parameter. It is important to note that we purposely begin with an array of $q_u$ values instead of m/z values for these very reasons.

Once an array of Mathieu $q_u$ values is chosen, they are converted to secular frequencies, which proceeds first through the calculation of the Mathieu $\beta_u$ parameter, $$\beta_u^2 = a_u + \cfrac{q_u^2}{(\beta_u + 2)^2 - a_u - \cfrac{q_u^2}{(\beta_u + 4)^2 - a_u - \cfrac{q_u^2}{(\beta_u + 6)^2 - a_u - \ldots}}} + \cfrac{q_u^2}{(\beta_u - 2)^2 - a_u - \cfrac{q_u^2}{(\beta_u - 4)^2 - a_u - \cfrac{q_u^2}{(\beta_u - 6)^2 - a_u - \ldots}}} \quad (8)$$

a conversion that can be done by using the algorithm described in Snyder et al. (Rapid Commun. Mass Spectrom. 2016, 30, 1190), the content of which is incorporated by reference herein in its entirety. The final step is to convert Mathieu $\beta_u$ values to secular frequencies (eqns. 9, 10) to give applied AC frequency vs time. Each ion has a set of secular frequencies, $$\omega_{u,n} = |2n + \beta_u| \Omega/2 \quad -\infty < n < \infty \quad (9)$$

where n is an integer, amongst which is the primary resonance frequency, the fundamental secular frequency, $$\omega_{u,0} = \beta_u \Omega/2 \quad (10)$$

This conversion gives an array of frequencies for implementation into a custom waveform calculated in a mathematics suite (e.g. Matlab).

Prior work used a logarithmic sweep of the AC frequency for secular frequency scanning, but, as described here, the relationship between secular frequency and m/z is not logarithmic, resulting in very high mass errors during mass calibration.

In theory, once the Mathieu $q_u$ parameters are converted to secular frequencies, a waveform is obtained. However, this waveform should not be used for secular frequency scanning due to the jagged edges observed throughout the waveform (i.e. phase discontinuities). In the mass spectra, this is observed as periodic spikes in the baseline intensities. Instead, in order to perform a smooth frequency scan, a new parameter $\Phi$ is introduced. This corresponds to the phase of the sinusoid at every time step (e.g. the $i^{th}$ phase in the waveform array, where i is an integer from 0 to $v*\Delta t-1$). Instead of scanning the frequency of the waveform, the phase of the sinusoid is instead scanned in order to maintain a continuous phase relationship. The relationship between ordinary (i.e. not angular) frequency f and phase $\Phi$ is:

$$f(t) = (\frac{1}{2}\lambda)(d\Phi/dt)(t) \quad (11)$$

so that $$\Phi(t) = \Phi(0) + 2\pi \int_0 f(\tau) d\tau \quad (12)$$

where variable $\tau$ has been substituted for time t in order to prevent confusion between the integration limit t and the time variable in the integrand. Thus, the phase of the sine wave at a given time t can be obtained by integrating the function that describes the frequency of the waveform as a function of time, which was previously calculated.

We begin with the phase of the waveform set equal to zero:

$$\Phi(0) = 0(t=0) \quad (13)$$

The phase is then incremented according to eqns. 14 and 15, which accumulates (integrates) the frequency of the sinusoid, so that $$\Delta = \omega_{u,0}/v \quad (14)$$

$$\Phi(i+1) = \Phi(i) + \Delta \quad (15)$$

where v is the sampling rate of the waveform generator. Note that $\omega_{u,0}$ is the angular secular frequency ($2*\pi*f_{u,0}$, where $f_{u,0}$ is the ordinary secular frequency in Hz) in units of radians/sec. Thus, sweeping through phase $\Phi$ instead of frequency gives a smooth frequency sweep.

Because the relationship between secular frequency and time is approximately an inverse function, the phase will be swept according to the integral of an inverse function, which is a logarithmic function. However, because the relationship between secular frequency and m/z is only approximately an inverse relationship, the phase $\Phi$ will deviate from the log function and thus cannot be described analytically (due to eq. 8).

Ion Traps and Mass Spectrometers

Any ion trap known in the art can be used in systems of the invention. Exemplary ion traps include a hyperbolic ion trap (e.g., U.S. Pat. No. 5,644,131, the content of which is incorporated by reference herein in its entirety), a cylindrical ion trap (e.g., Bonner et al., International Journal of Mass Spectrometry and Ion Physics, 24(3):255-269, 1977, the content of which is incorporated by reference herein in its entirety), a linear ion trap (Hagar, Rapid Communications in Mass Spectrometry, 16(6):512-526, 2002, the content of which is incorporated by reference herein in its entirety), and a rectilinear ion trap (U.S. Pat. No. 6,838,666, the content of which is incorporated by reference herein in its entirety).

Any mass spectrometer (e.g., bench-top mass spectrometer of miniature mass spectrometer) may be used in systems of the invention and in certain embodiments the mass spectrometer is a miniature mass spectrometer. An exemplary miniature mass spectrometer is described, for example in Gao et al. (Anal. Chem. 2008, 80, 7198-7205.), the content of which is incorporated by reference herein in its entirety. In comparison with the pumping system used for lab-scale instruments with thousands of watts of power, miniature mass spectrometers generally have smaller pumping systems, such as a 18 W pumping system with only a 5 L/min (0.3 m³/hr) diaphragm pump and a 11 L/s turbo pump for the system described in Gao et al. Other exemplary miniature mass spectrometers are described for example in Gao et al. (Anal. Chem., 2008, 80, 7198-7205.), Hou et al. (Anal. Chem., 2011, 83, 1857-1861.), and Sokol et al. (Int. J. Mass Spectrom., 2011, 306, 187-195), the content of each of which is incorporated herein by reference in its entirety.

Figure 10:
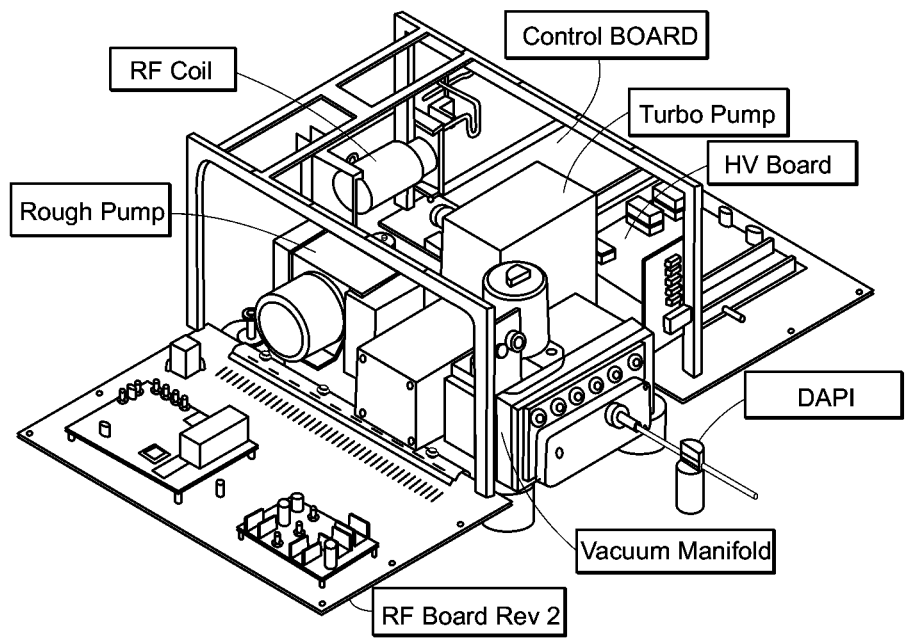
FIG. 10 is a picture illustrating various components and their arrangement in a miniature mass spectrometer.

FIG. 10 is a picture illustrating various components and their arrangement in a miniature mass spectrometer. The control system of the Mini 12 (Linfan Li, Tsung-Chi Chen, Yue Ren, Paul I. Hendricks, R. Graham Cooks and Zheng Ouyang "Miniature Ambient Mass Analysis System" Anal.

Chem. 2014, 86 2909-2916, DOI: 10.1021/ac403766c; and 860. Paul I. Hendricks, Jon K. Dalgleish, Jacob T. Shelley, Matthew A. Kirleis, Matthew T. McNicholas, Linfan Li, Tsung-Chi Chen, Chien-Hsun Chen, Jason S. Duncan, Frank Boudreau, Robert J. Noll, John P. Denton, Timothy A. Roach, Zheng Ouyang, and R. Graham Cooks "Autonomous in-situ analysis and real-time chemical detection using a backpack miniature mass spectrometer: concept, instrumentation development, and performance" Anal. Chem., 2014, 86 2900-2908 DOI: 10.1021/ac403765x, the content of each of which is incorporated by reference herein in its entirety), and the vacuum system of the Mini 10 (Liang Gao, Qingyu Song, Garth E. Patterson, R. Graham Cooks and Zheng Ouyang, "Handheld Rectilinear Ion Trap Mass Spectrometer", Anal. Chem., 78 (2006) 5994-6002 DOI: 10.1021/ac061144k, the content of which is incorporated by reference herein in its entirety) may be combined to produce the miniature mass spectrometer shown in FIG. 10. It may have a size similar to that of a shoebox (H20×W25 cm×D35 cm). In certain embodiments, the miniature mass spectrometer uses a dual LIT configuration, which is described for example in Owen et al. (U.S. patent application Ser. No. 14/345,672), and Ouyang et al. (U.S. patent application Ser. No. 61/865,377), the content of each of which is incorporated by reference herein in its entirety.

Ionization Sources

In certain embodiments, the systems of the invention include an ionizing source, which can be any type of ionizing source known in the art. Exemplary mass spectrometry techniques that utilize ionization sources at atmospheric pressure for mass spectrometry include paper spray ionization (ionization using wetted porous material, Ouyang et al., U.S. patent application publication number 2012/0119079), electrospray ionization (ESI; Fenn et al., Science, 1989, 246, 64-71; and Yamashita et al., J. Phys. Chem., 1984, 88, 4451-4459.); atmospheric pressure ionization (APCI; Carroll et al., Anal. Chem. 1975, 47, 2369-2373); and atmospheric pressure matrix assisted laser desorption ionization (AP-MALDI; Laiko et al. Anal. Chem., 2000, 72, 652-657; and Tanaka et al. Rapid Commun. Mass Spectrom., 1988, 2, 151-153,). The content of each of these references is incorporated by reference herein in its entirety.

Exemplary mass spectrometry techniques that utilize direct ambient ionization/sampling methods include desorption electrospray ionization (DESI; Takats et al., Science, 2004, 306, 471-473, and U.S. Pat. No. 7,335,897); direct analysis in real time (DART; Cody et al., Anal. Chem., 2005, 77, 2297-2302.); atmospheric pressure dielectric barrier discharge Ionization (DBDI; Kogelschatz, Plasma Chemistry and Plasma Processing, 2003, 23, 1-46, and PCT international publication number WO 2009/102766), and electrospray-assisted laser desorption/ionization (ELDI; Shiea et al., J. Rapid Communications in Mass Spectrometry, 2005, 19, 3701-3704.). The content of each of these references in incorporated by reference herein its entirety.

System Architecture

Figure 11:
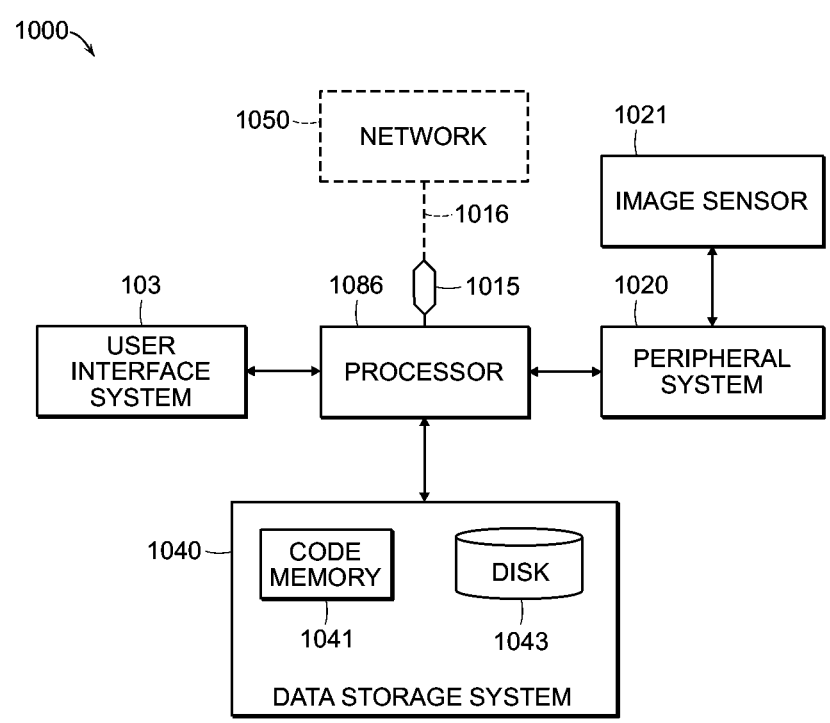
FIG. 11 shows a high-level diagram of the components of an exemplary data-processing system for analyzing data and performing other analyses described herein, and related components.

FIG. 11 is a high-level diagram showing the components of an exemplary data-processing system 1000 for analyzing data and performing other analyses described herein, and related components. The system includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The data described above may be obtained using detector 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 which in one embodiment may be capable of real-time calculations (and in an alternative embodiment configured to perform calculations on a non-real-time basis and store the results of calculations for use later) can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (e.g., a tablet) connected, e.g., via a network or a null-modem cable, or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), Universal Serial Bus (USB) interface memory device, erasable programmable read-only memories (EPROM, EEPROM, or Flash), remotely accessible hard drives, and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects. These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors) to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Discontinuous Atmospheric Pressure Interface (DAPI)

In certain embodiments, the systems of the invention can be operated with a Discontinuous Atmospheric Pressure Interface (DAPI). A DAPI is particularly useful when coupled to a miniature mass spectrometer, but can also be used with a standard bench-top mass spectrometer. Discontinuous atmospheric interfaces are described in Ouyang et al. (U.S. Pat. No. 8,304,718 and PCT application number PCT/US2008/065245), the content of each of which is incorporated by reference herein in its entirety.

Samples

A wide range of heterogeneous samples can be analyzed, such as biological samples, environmental samples (including, e.g., industrial samples and agricultural samples), and food/beverage product samples, etc.

Exemplary environmental samples include, but are not limited to, groundwater, surface water, saturated soil water, unsaturated soil water; industrialized processes such as waste water, cooling water; chemicals used in a process, chemical reactions in an industrial processes, and other systems that would involve leachate from waste sites; waste and water injection processes; liquids in or leak detection around storage tanks; discharge water from industrial facilities, water treatment plants or facilities; drainage and leachates from agricultural lands, drainage from urban land uses such as surface, subsurface, and sewer systems; waters from waste treatment technologies; and drainage from mineral extraction or other processes that extract natural resources such as oil production and in situ energy production.

Additionally exemplary environmental samples include, but certainly are not limited to, agricultural samples such as crop samples, such as grain and forage products, such as soybeans, wheat, and corn. Often, data on the constituents of the products, such as moisture, protein, oil, starch, amino acids, extractable starch, density, test weight, digestibility, cell wall content, and any other constituents or properties that are of commercial value is desired.

Exemplary biological samples include a human tissue or bodily fluid and may be collected in any clinically acceptable manner. A tissue is a mass of connected cells and/or extracellular matrix material, e.g. skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sputum, sweat, amniotic fluid, menstrual fluid, mammary fluid, peritoneal fluid, urine, semen, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed.

In one embodiment, the biological sample can be a blood sample, from which plasma or serum can be extracted. The blood can be obtained by standard phlebotomy procedures and then separated. Typical separation methods for preparing a plasma sample include centrifugation of the blood sample. For example, immediately following blood draw, protease inhibitors and/or anticoagulants can be added to the blood sample. The tube is then cooled and centrifuged, and can subsequently be placed on ice. The resultant sample is separated into the following components: a clear solution of blood plasma in the upper phase; the buffy coat, which is a thin layer of leukocytes mixed with platelets; and erythrocytes (red blood cells). Typically, 8.5 mL of whole blood will yield about 2.5-3.0 mL of plasma.

Blood serum is prepared in a very similar fashion. Venous blood is collected, followed by mixing of protease inhibitors and coagulant with the blood by inversion. The blood is allowed to clot by standing tubes vertically at room temperature. The blood is then centrifuged, wherein the resultant supernatant is the designated serum. The serum sample should subsequently be placed on ice.

Prior to analyzing a sample, the sample may be purified, for example, using filtration or centrifugation. These techniques can be used, for example, to remove particulates and chemical interference. Various filtration media for removal of particles includes filer paper, such as cellulose and membrane filters, such as regenerated cellulose, cellulose acetate, nylon, PTFE, polypropylene, polyester, polyethersulfone, polycarbonate, and polyvinylpyrolidone. Various filtration media for removal of particulates and matrix interferences includes functionalized membranes, such as ion exchange membranes and affinity membranes; SPE cartridges such as silica- and polymer-based cartridges; and SPE (solid phase extraction) disks, such as PTFE- and fiberglass-based. Some of these filters can be provided in a disk format for loosely placing in filter holdings/housings, others are provided within a disposable tip that can be placed on, for example, standard blood collection tubes, and still others are provided in the form of an array with wells for receiving pipetted samples. Another type of filter includes spin filters. Spin filters consist of polypropylene centrifuge tubes with cellulose acetate filter membranes and are used in conjunction with centrifugation to remove particulates from samples, such as serum and plasma samples, typically diluted in aqueous buffers.

Filtration is affected in part, by porosity values, such that larger porosities filter out only the larger particulates and smaller porosities filtering out both smaller and larger porosities. Typical porosity values for sample filtration are the 0.20 and 0.45 μm porosities. Samples containing colloidal material or a large amount of fine particulates, considerable pressure may be required to force the liquid sample through the filter. Accordingly, for samples such as soil extracts or wastewater, a pre-filter or depth filter bed (e.g. "2-in-1" filter) can be used and which is placed on top of the membrane to prevent plugging with samples containing these types of particulates.

In some cases, centrifugation without filters can be used to remove particulates, as is often done with urine samples. For example, the samples are centrifuged. The resultant supernatant is then removed and frozen.

After a sample has been obtained and purified, the sample can be analyzed to determine the concentration of one or more target analytes, such as elements within a blood plasma sample. With respect to the analysis of a blood plasma sample, there are many elements present in the plasma, such as proteins (e.g., Albumin), ions and metals (e.g., iron), vitamins, hormones, and other elements (e.g., bilirubin and uric acid). Any of these elements may be detected using methods of the invention. More particularly, methods of the invention can be used to detect molecules in a biological sample that are indicative of a disease state.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Materials and Methods

Chemicals: All drug standards were purchased from Cerilliant (Round Rock, TX, USA) and were either used as provided or diluted in 50:50 methanol/water with 0.1% formic acid. All other standards were purchased from Sigma (St. Louis, MO, USA) and prepared similarly.

Ionization: Nanoelectrospray ionization was used for all experiments herein. In order to generate ions, 1.5 kV was applied to a nanospray electrode holder (glass size 1.5 mm), which was purchased from Warner Instruments (Hamden, CT, U.S.A.) and fitted with 0.127 mm diameter silver wire, part number 00303 (Alfa Aesar, Ward Hill, MA.). Borosilicate glass capillaries (1.5 mm O.D., 0.86 mm I.D.) from Sutter Instrument Co. (Novato, CA, U.S.A.) were pulled to 2 μm tip diameters using a Flaming/Brown micropipette puller (model P-97, Sutter Instrument Co.).

Instrumentation: All data was generated on a Thermo LTQ linear quadrupole ion trap (San Jose, CA, USA). The LTQ ion trap has an rf frequency of 1.166 MHz and dimensions of $x_0$=4.75 mm, $y_0$=4 mm, axial sections of length 12, 37, and 12 mm. See Schwartz, J. C.; Senko, M. W.; Syka, J. E. J. Am. Soc. Mass Spectrom. 2002, 13, 659-669, the content of which is incorporated by reference herein in its entirety. In these experiments, the rf amplitude was constant throughout injection, cooling, and mass scan stages, as described in Snyder, D. T.; Cooks, R. G. Anal. Chem. 2017, 89, 8148-8155, the content of which is incorporated by reference herein in its entirety. Because the mass range is limited when the rf amplitude is not varied (ions at low q are not generally useful), the experiments were subdivided into a low mass' mode (LMCO=73 Th) and a 'high mass' mode (LMCO=105 Th). The LTQ used in this work was previously modified to be able to apply low voltage ac signals to both the x and y rods. The data collection rate in the 'normal' scan rate mode with 'high' selected as the mass range was 28.732 kHz, which is fixed by the LTQ data system and cannot be changed (but does vary between different scan modes). The helium normally used in the LTQ was substituted with nitrogen at an ion gauge reading of $1.4 \times 10^{-5}$ torr. Nitrogen increases fragmentation efficiency but also decreases resolution.

Waveform Generation: Two waveforms were used in these experiments; both were calculated in Matlab (Mathworks, Natick, MA, USA), exported as .csv files and imported into one of two Keysight 33612A arbitrary waveform generators (purchased from Newark element14, Chicago, IL, USA) with 64 megasample memory upgrades. One generator supplied the waveform for precursor ion excitation in the y dimension while the other supplied a broadband sum of sines for product ion ejection in the x dimension.

A first waveform was a frequency sweep applied in the y dimension of the LTQ ion trap in order to mass-selectively fragment precursor ions as a function of time. The frequency sweep was an inverse Mathieu q scan (nonlinear frequency sweep with linear mass scale vs. time) from Mathieu $q=0.908$ to $q=0.15$ over 600 ms, which is described foe example in Snyder, D. T.; Pulliam, C. J.; Cooks, R. G. Rapid Commun. Mass Spectrom. 2016, 30, 2369-2378, the content of which is incorporated by reference herein in its entirety. This excitation sweep always had a peak-to-peak amplitude of 350 $mV_{pp}$.

The second waveform, constructed as described below and applied in the x dimension, was a broadband sum of sines used to eject all product ions of the excited precursor ions; the product ions' m/z values were encoded in the beats in the waveform so that beat frequency and product ion secular frequency were directly proportional. A master array contained main frequencies that were spaced every 10 kHz from Mathieu $q=0.908$ to $q=0.15$, with the lowest frequency being 73 kHz. Beat frequencies were then encoded by adding a second frequency per main frequency, with a starting beat frequency of 500 Hz and subsequent spacings of 600 Hz, 700 Hz, 800 Hz, etc (i.e. the beat increased by 100 Hz per 10 kHz). The lowest main frequencies (corresponding to the highest m/z ions) had the smallest beat frequencies, and the highest main frequencies (lowest m/z ions) had the highest beat frequencies. The frequencies in the waveform were therefore 73 kHz and 73.5 kHz, 83 kHz and 83.6 kHz, 93 kHz and 93.7 kHz, and so on until half the rf frequency was met. Phase overmodulation using a quadratic function of phase vs. frequency (common with Stored Waveform Inverse Fourier Transform methods) was used to maintain an approximately constant voltage amplitude (6 $V_{pp}$) as a function of time. The ejection waveform was built point-by-point, and, critically, only frequencies at least 10 kHz above the precursor ion's frequency were included in each point. That is, the frequency components of the sum of sines waveform varied because the excited precursor ion mass varied and thus the product ion mass range varied as a function of time. The excited precursor ion's frequency is known because it equals the frequency applied by the excitation waveform (the inverse Mathieu q scan). For example, if at time 0.1 s the inverse Mathieu q scan is applying a frequency of 300 kHz to fragment a precursor ion, then at that time point the sum of sines waveform will only include frequencies above 310 kHz.

This particular waveform was not the only waveform that successfully encoded product ion frequencies. The main frequency spacing can be altered from 10 kHz and the difference between adjacent beat frequencies (100 Hz in this work) can also be altered. Moreover, there need not be 'main frequencies.' For example, one could encode the frequencies as follows: 73 kHz, 73.5 kHz (+0.5 kHz compared to adjacent frequency), 74.1 kHz (+0.6 kHz), 74.8 kHz (+0.7 kHz), 75.6 kHz (+0.8 kHz), and so on. Several different waveforms were successful, but we will only show data for the particular encoding described in the previous paragraphs.

All mass and frequency spectra are the result of an average of 10 scans. Fast Fourier transforms were calculated in Matlab using 301 points per peak and a sampling rate of 28.732 kHz, as described previously. Only frequencies above 300 Hz are shown in the spectra and used for statistical analysis. Peaks below this frequency correspond to the width of each mass peak which is not useful. Software precursor ion scans were also performed in Matlab after the total ion current in the frequency spectra was normalized to 1. Principal component analysis (PCA) was conducted in OriginPro 2018 (OriginLab Corporation, Northampton, MA, USA) using built-in PCA tools.

Example 2: Program for Building a Frequency Tagged Broadband Waveform for Use Alongside an Inverse Mathieu Q Scan

```
% Program for building a frequency tagged broadband waveform for use with the %
corresponding inverse Mathieu q scan
% Define variables
scan_time = .6;              % scan time in seconds
begin_q = 0.908;             % Starting Mathieu q value of the inverse q scan
end_q = 0.15;                % Ending Mathieu q value of the inverse q scan
sampling_rate = 5000000;     % sampling rate of wavefor
rf_frequency = 1166000;      % tuned rf frequency in Hz
num_points = ceil(sampling_rate * scan_time); % number of points in waveform
time = linspace(0, num_points-1, num_points)*scan_time/num_points;
% time variable
frequency_resolution = 10000; % spacing between main frequencies (Hz)
first_beat_freq_Hz = 500;    % smallest beat frequency
beat_freq_spacing_Hz = 100;  % spacing between beat frequencies
distance_from_lower_bound = 10000; % space between lower frequency bound and
                             % lowest frequency in broadband signal
                             % (Hz)
phase_fudge_factor = 0.0001; % used for phase overmodulation to keep
                             % amplitude of waveform
                             % approximately constant
% Calculate Mathieu q values as a function of time
% assume sweep according to q = k / (t−j)
% The array 'q_values' tells us which precursor ion is being fragmented at
% any given time. We need to know this because the product ions of this
% precursor ion will always have frequencies higher than the precursor,
% assuming the ions are singly charged.
```

```
j = end_q*scan_time / (end_q - begin_q);
k = -begin_q*j;
q_values = k ./ (time - j);
% Calculate the frequency lower bound (i.e. the frequency of the excited
% precursor ions) as a function of time from Mathieu q
% values and rf frequency.
% We need the frequencies in the broadband waveform to always be above the
% lower bound because the product ion mass range - and thus frequency range -
% varies as a function of time (because the precursor ions are fragmented
% from low to high m/z) and thus the frequencies in the broadband
% waveform must also vary with time.
lower_bound_frequencies = zeros(num_points,1);
betas = zeros(num_points,1);
for i = 1:num_points
    betas(i) = beta_calculator(q_values(i));
    lower_bound_frequencies(i) = betas(i)*rf_frequency/2;
end
% Build frequencies array
num_frequencies = floor(abs(rf_frequency/2-
lower_bound_frequencies(end))/frequency_resolution);
% total number of frequencies in waveform
main_frequencies = linspace(rf_frequency/2,rf_frequency/2-
num_frequencies*frequency_resolution+frequency_resolution,num_frequencies);
main_frequencies = fliplr(main_frequencies);
% Add in beat frequencies to encode product ion m/z
for i=1:num_frequencies
    frequencies(2*i-1) = main_frequencies(i);
    frequencies(2*i) = main_frequencies(i) + first_beat_freq_Hz + (i-1)*beat_freq_spacing_Hz;
end
frequencies = fliplr(frequencies);
% Distribute phases so that master waveform has flat amplitude profile
phases = zeros(length(frequencies),1);
for i=1:length(frequencies)
    phases(i) = (frequencies(i)-frequencies(1))^2*scan_time/(2*(frequencies(num_frequencies)-
frequencies(1))*phase_fudge_factor);
end
% Build final waveform point by point, making sure to exclude frequencies
% below the precursor ion frequency
waveform = zeros(num_points,1);
for i=1:num_points
    for n=1:length(frequencies)
        if (frequencies(n) > lower_bound_frequencies(i) +
distance_from_lower_bound)
waveform(i) = waveform(i)+sin(2*pi*frequencies(n)*time(i)+phases(n));
        else
            break;
        end
    end
end
```

What is claimed is:

1. A method for analyzing a sample, the method comprising:

introducing a precursor ion of a sample into a mass spectrometer comprising a single ion trap; and analyzing the sample via the mass spectrometer that applies a plurality of scan functions to the single ion trap to fragment the precursor ion and simultaneously eject a product ion of the precursor ion in a manner that preserves in time a relationship of the precursor ion and the product ion.

* * * * *